United States Patent [19]
Clark

[11] Patent Number: 5,700,794
[45] Date of Patent: Dec. 23, 1997

[54] TREATMENT OF OCULAR HYPOTONY

[75] Inventor: Abbot F. Clark, Arlington, Tex.

[73] Assignee: Alcon Laboratories Inc., Fort Worth, Tex.

[21] Appl. No.: 674,303

[22] Filed: Jul. 1, 1996

Related U.S. Application Data

[63] Continuation of Ser. No. 322,814, Oct. 13, 1994, abandoned.

[51] Int. Cl.$^6$ ..................................................... A61K 31/56
[52] U.S. Cl. ............................................. 514/177; 514/912
[58] Field of Search ..................................... 514/177, 912

[56] References Cited

PUBLICATIONS

Starka, et al., *Aldosterone: Its Occurrence, Metabolism and Binding in the Rabbit Eye*, Exp. Eye Res., 25, 91–98 (1977).

Starka, et al., *Aldosterone Binding in Bovine Ciliary Body*, Endocrinologia Experimentalis, 11, 203–208 (1977).

Panigrahy, et al., *Modulation of Intraocular Pressure by Aldosterone and Spironolactone*, Investigative Ophthalmology & Visual Science, 35:4, 1388 (Mar. 15, 1994).

Frenkel, et al., *Effects of Two Mineralocorticoids on Ocular Tension*, Archives of Ophthalmology, 72, 315–318 (1964).

Marver, et al., *Dihydrocortisol: A Potential Mineralocorticoid*, Journal of Steroid Biochemistry, 9, 1–7 (1978).

Medline Abstract of Science (1983 Oct. 14) 222 (4620) 172–3. Weinstein et al.

*Primary Examiner*—Zohreh Fay
*Attorney, Agent, or Firm*—Sally Yeager

[57] ABSTRACT

Methods for treating ocular hypotony are disclosed.

4 Claims, No Drawings

TREATMENT OF OCULAR HYPOTONY

This application is a continuation of application Ser. No. 08/322,814, filed Oct. 13, 1994 now abandoned.

FIELD OF THE INVENTION

This invention is directed to the use of mineralocorticoids to treat ocular hypotony.

BACKGROUND OF THE INVENTION

It has been suggested that mineralocorticoids may be associated with ocular dynamics by increasing the rate of aqueous humor formation. The endogenous mineralocorticoid, aldosterone, has been found in the aqueous humor, see Starka, et al., *Aldosterone: Its Occurrence, Metabolism and Binding in the Rabbit Eye*, Exp. Eye Res., Vol. 25, pp. 91–98 (1977); and mineralocorticoid receptors have been found in the ciliary process, see Starka, et al., cited above and Starka, et al., *Aldosterone Binding in Bovine Ciliary Body*, Endocrinologia Experimentalis, Vol. 11, pp. 203–208 (1977). Panigrahy, et al. showed that endogenous aldosterone is involved in the regulation of intraocular pressure in the rabbit eye, see *Modulation of Intraocular Pressure by Aldosterone and Spironolactone*, Investigative Ophthalmology & Visual Science, Vol. 35, No. 4, p. 1388 (Mar. 15, 1994). The results of a study by Frenkel, et al. in *Effects of Two Mineralocorticoids on Ocular Tension*, Archives of Ophthalmology, Vol. 72, pp. 315–318 (1964) suggests that systemic mineralocorticoids can increase aqueous influx in the eye and produce a rise in ocular tension in some glaucoma patients.

SUMMARY OF THE INVENTION

This invention is directed to a method for treating ocular hypotony by the topical application of mineralocorticoids.

DETAILED DESCRIPTION OF THE PREFERRED EMBODIMENTS

Ocular hypotony is a condition of reduced tension in the eye. It can be a serious complication in glaucoma treatment, for example, following glaucoma filtration surgery. In addition, in some glaucoma patients, the drugs used to control the patient's intraocular pressure can lower the pressure to the point that the eye globe partially collapses.

There is currently no effective method for pharmacologically treating ocular hypotony. Generally, the condition remains untreated or intraocular injections of a viscous substance, such as, sodium hyaluronate are used. The topical use of mineralocorticoids to treat hypotony provides a preferred method for treating the condition.

The mineralocorticoids are included in formulations that can be applied topically to the eye of warm-blooded animals, such as solutions, suspensions, gels, or ointments. They are present in the formulations at concentrations of from 0.05–5.0 weight percent (wt. %). The formulations can include other components known to those skilled in the art of formulating ophthalmic products. For example, the formulations can include ophthalmically acceptable preservatives, surfactants, viscosity enhancers, penetration enhancers, and buffers. The formulations are administered topically to the eye as needed to reach and maintain the appropriate intraocular pressure according to the routine discretion of the skilled clinician.

Preferred mineralocorticoids include aldosterone, dihydrocortisol (which has mineralocorticoid activity, see Marver, et al., *Dihydrocortisol: A Potential Mineratocorticoid*, Journal of Steroid Biochemistry, Vol. 9, pp. 1–7 (1978)), fludrocortisone, and 11-desoxycorticosterone. Most preferred is aldosterone. The structures for these compounds are set forth below.

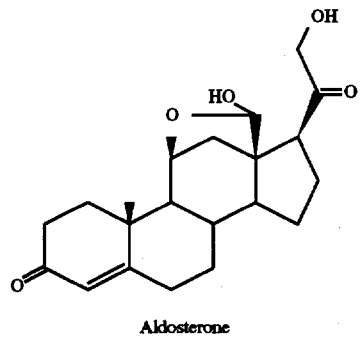

Aldosterone

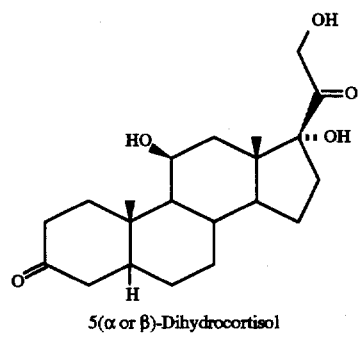

5(α or β)-Dihydrocortisol

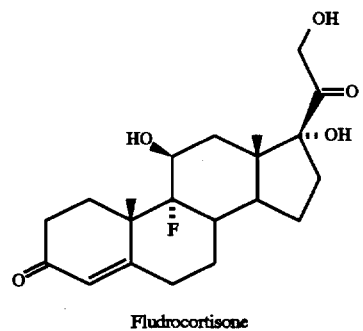

Fludrocortisone

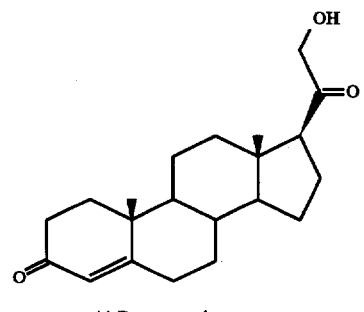

11-Desoxycorticosterone

The following examples are illustrative of the types of formulations which are useful in treating ocular hypotony, they are not meant to be limiting.

EXAMPLE 1

| Component | wt. % |
| --- | --- |
| 5-Dihydrocortisol | 1.00% |
| Mannitol | 2.40% |
| Sodium chloride | 0.40% |
| Carbopol 974P | 0.50% |
| Polysorbate 80 | 0.05% |
| Edetate disodium | 0.01% |
| Benzalkonium chloride | 0.01% + 5% XS |
| Sodium hydroxide | adjust pH to 7.2 |
| Purified water | qs to 100% |

This formulation is made according to methods known to those skilled in the art of ophthalmic pharmaceuticals formulation.

EXAMPLE 2

| Component | wt. % |
| --- | --- |
| Aldosterone | 1.0% |
| Tyloxapol | 0.01–0.05% |
| HPMC | 0.5% |
| Benzalkonium chloride | 0.01% |
| Sodium chloride | 0.8% |
| Edetate disodium | 0.01% |
| NaOH/HCl | q.s. pH 7.4 |
| Purified water | q.s. 100 mL |

The above formulation is prepared by first placing a portion of the purified water into a beaker and heating to 90° C. The hydroxypropylmethylcellulose (HPMC) is then added to the heated water and mixed by means of vigorous vortex stirring until all of the HPMC is dispersed. The resulting mixture is then allowed to cool while undergoing mixing in order to hydrate the HPMC. The resulting solution is then sterilized by means of autoclaving in a vessel having a liquid inlet and a hydrophobic, sterile air vent filter.

The sodium chloride and the edetate disodium are then added to a second portion of the purified water and dissolved. The benzalkonium chloride is then added to the solution, and the pH of the solution is adjusted to 7.4 with 0.1M NaOH/HCl. The solution is then sterilized by means of filtration.

Aldosterone is sterilized by either dry heat or ethylene oxide. If ethylene oxide sterilization is selected, aeration for at least 72 hours at 50° C. is necessary. The sterilized steroid is weighed aseptically and placed into a pressurized ballmill container. The tyloxapol, in sterilized aqueous solution form, is then added to the ballmill container. Sterilized glass balls are then added to the container and the contents of the container are milled aseptically at 225 rpm for 16 hours, or until all particles are in the range of approximately 5 microns.

Under aseptic conditions, the micronized drug suspension formed by means of the preceding step is then poured into the HPMC solution with mixing. The ballmill container and balls contained therein are then rinsed with a portion of the solution containing the sodium chloride, the edetate disodium and benzalkonium chloride. The rinse is then added aseptically to the HPMC solution. The final volume of the solution is then adjusted with purified water and, if necessary, the pH of the solution is adjusted to pH 7.4 with NaOH/HCl.

I claim:

1. A method for treating ocular hypotony by administering topically to the eye a pharmaceutically effective amount of a mineralocorticoid.

2. The method of claim 1 wherein the mineralocorticoid is selected from the group consisting of aldosterone, dihydrocortisol, fludrocortisone, and 11-desoxycorticosterone.

3. The method of claim 2 wherein the mineralocorticoid is aldosterone.

4. The method of claim 1 wherein the mineralocorticoid is present at a concentration of 0.05–5 wt. %.

* * * * *